(12) United States Patent
Akahane et al.

(10) Patent No.: US 7,030,121 B2
(45) Date of Patent: Apr. 18, 2006

(54) PYRAZOLOPYRAZINE COMPOUND AND PHARMACEUTICAL USE THEREOF

(75) Inventors: Atsushi Akahane, Osaka (JP); Akira Tanaka, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 218 days.

(21) Appl. No.: 10/479,622

(22) PCT Filed: Jun. 3, 2002

(86) PCT No.: PCT/JP02/05453

§ 371 (c)(1),
(2), (4) Date: Dec. 4, 2003

(87) PCT Pub. No.: WO02/100864

PCT Pub. Date: Dec. 19, 2002

(65) Prior Publication Data

US 2004/0152706 A1     Aug. 5, 2004

(30) Foreign Application Priority Data

Jun. 6, 2001 (AU) .................................. PR 5486

(51) Int. Cl.
| A01N 43/58 | (2006.01) |
| A01N 43/60 | (2006.01) |
| A61K 31/495 | (2006.01) |
| A61K 31/50 | (2006.01) |
| C07D 471/00 | (2006.01) |

(52) U.S. Cl. ...................................... 514/249; 544/350
(58) Field of Classification Search .................... None
See application file for complete search history.

(56) References Cited

U.S. PATENT DOCUMENTS

| 4,925,849 A | 5/1990 | Shiokawa et al. |
| 4,985,444 A | 1/1991 | Shiokawa et al. |
| 4,994,453 A | 2/1991 | Shiokawa et al. |
| 5,087,629 A | 2/1992 | Shiokawa et al. |
| 5,102,869 A | 4/1992 | Shiokawa et al. |
| 5,102,878 A | 4/1992 | Shiokawa et al. |
| 5,155,114 A | 10/1992 | Shiokawa et al. |
| 5,179,103 A | 1/1993 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,338,743 A | 8/1994 | Shiokawa et al. |
| 5,773,530 A | 6/1998 | Akahane et al. |
| 6,124,456 A | 9/2000 | Akahane et al. |
| 6,355,640 B1 | 3/2002 | Akahane et al. |

FOREIGN PATENT DOCUMENTS

| EP | 0 299 209 | 1/1989 |
| EP | 0 379 979 | 8/1990 |
| EP | 0 467 248 | 1/1992 |
| EP | 1 177 797 | 2/2002 |
| WO | 01 40230 | 6/2001 |

OTHER PUBLICATIONS

Guieu et al, "Adenosine and the Nervous System: Clinical impications" Clinical Neuropharmacology, vol. 19(6), pp. 459-474 (1996).*

* cited by examiner

Primary Examiner—James O. Wilson
Assistant Examiner—Zachary C. Tucker
(74) Attorney, Agent, or Firm—Oblon, Spivak, McClelland, Maier & Neustadt, P.C.

(57) ABSTRACT

A pyrazolopyrazine compound of the following formula (I).

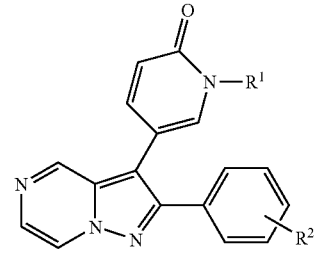

(I)

wherein
$R^1$ is hydrogen or a suitable substituent; and
$R^2$ is hydrogen or halogen,
or a salt thereof.

The pyrazolopyrazine compound (I) and salt thereof of the present invention are adenosine antagonists and are useful for the prevention and/or treatment of depression, dementia (e.g. Alzheimer's disease, cerebrovascular dementia, dementia accompanying Parkinson's disease, etc.), Parkinson's disease, anxiety, pain, cerebrovascular disease (e.g. stroke, etc.), heart failure and the like.

6 Claims, No Drawings

PYRAZOLOPYRAZINE COMPOUND AND PHARMACEUTICAL USE THEREOF

TECHNICAL FIELD

The present invention relates to a novel pyrazolopyrazine compound and a salt thereof, which are useful as medicaments.

BACKGROUND ART

Some pyrazolopyridine compounds to be useful as psychostimulant, remedy for renal failure, or the like are known (e.g. EP-0299209, EP-0379979, EP-0467248, EP-0516941, etc.). Pyrazolopyrazine compounds having pyridazine group to be adenosine antagonists are also known (WO00/69464). However, pyrazolopyrazine compounds having pyridine group are novel, so there has been no knowledge about these compounds.

DISCLOSURE OF INVENTION

The present invention relates to a novel pyrazolopyrazine compound and a pharmaceutically acceptable salt thereof, which are useful as medicaments; processes for the preparation of said pyrazolopyrazine compound and a salt thereof; a pharmaceutical composition comprising, as an active ingredient, said pyrazolopyrazine compound or a pharmaceutically acceptable salt thereof; a use of said pyrazolopyrazine compound or a pharmaceutically acceptable salt thereof as a medicament; and a method for using said pyrazolopyrazine compound or a pharmaceutically acceptable salt thereof for therapeutic purposes, which comprises administering said pyrazolopyrazine compound or a pharmaceutically acceptable salt thereof to a human being or an animal.

The pyrazolopyrazine compound and a salt thereof are adenosine antagonists (especially, $A_1$ receptor and $A_2$ (particularly A2a) receptor dual antagonists) and possess various pharmacological actions such as anticatalepsy action, cognitive enhancing action, analgesic action, locomotor action, antidepressant action, diuretic action, cardioprotective action, cardiotonic action, vasodilating action (e.g. cerebral vasodilating action, etc.), the action of increasing the renal blood flow, renal protective action, improvement action of renal function, enhancing action of lipolysis, inhibition action of anaphylactic bronchoconstriction, acceleration action of the insulin release, the action of increasing the production of erythropoietin, inhibiting action of platelet aggregation, or the like.

They are useful as cognitive enhancer, antianxietry drug, antidementia drug, psychostimulant, analgesic, cardioprotective agent, antidepressant, ameliorants of cerebral circulation, tranquilizer, drug for heart failure, cardiotonic agent, antihypertensive agent, drug for renal failure (renal insufficiency), drug for renal toxicity, renal protective agent, drug for improvement of renal function, diuretic, drug for edema, antiobesity, antiasthmatic, bronchodilator, drug for apnea, drug for gout, drug for hyperuricemia, drug for sudden infant death syndrome (SIDS), ameliorants of immunosuppressive action of adenosine, antidiabetic agent, drug for ulcer, drug for pancreatitis, drug for Meniere's syndrome, drug for anemia;

drug for thrombosis, drug for myocardial infarction, drug for obstruction, drug for arteriosclerosis obliterans, drug for thrombophlebitis, drug for cerebral infarction, drug for transient ischemic attack, drug for angina pectoris, or the like;

and useful for the prevention and/or treatment of depression, dementia (e.g. Alzheimer's disease, cerebrovascular dementia, dementia accompanying Parkinson's disease, etc.), Parkinson's disease, anxiety, pain, cerebrovascular disease (e.g. stroke, etc.), heart failure;

hypertension (e.g. essential hypertension, nephrogenous hypertension, etc.);

circulatory insufficiency (acute circulatory insufficiency) cuased by, for example, ischemia/reperfusion injury (e.g. myocardial ischemia/reperfusion injury, cerebral ischemia/reperfusion injury, peripheral ischemia/reperfusion injury, etc.), shock (e.g. endotoxin shock, hemorrhagic shock, etc.), surgical procedure, or the like; post-resuscitation asystole;

bradyarrhythmia;

electro-mechanical dissociation;

hemodynamic collapse;

SIRS (systemic inflammatory response syndrome);

multiple organ failure;

renal failure (renal insufficiency) (e.g. acute renal failure, etc.), renal toxicity [e.g. renal toxicity induced by a drug such as cisplatins, gentamicin, FR-900506 (disclosed in EP-0184162), cyclosporin (e.g. cyclosporin A) or the like; glycerol, etc.], nephrosis, nephritis, edema (e.g. cardiacedema, nephrotic edema, hepatic edema, idiopathic edema, drug edema, acute angioneurotic edema, hereditary angioneurotic edema, carcinomatous ascites, gestational edema, etc.);

obesity, bronchial asthma, gout, hyperuricemia, sudden infant death syndrome, immunosuppression, diabetes, ulcer suchaspeptic ulcer (e.g. gastric ulcer, duodenal ulcer, etc.), pancreatitis, Meniere's syndrome, anemia, dialysis-induced hypotension, constipation, ischemic bowel disease, ileus (e.g. mechanical ileus, adynamic ileus, etc.); and myocardial infarction, thrombosis (e.g. arterial thrombosis, cerebral thrombosis, etc.), obstruction, arteriosclerosis obliterans, thrombophlebitis, cerebral infarction, transient ischemic attack, angina pectoris, or the like.

The novel pyrazolopyrazine compound of the present invention can be shown by the following formula (I).

wherein

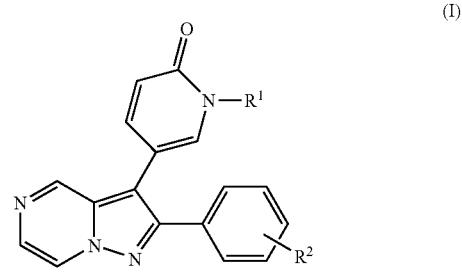

(I)

$R^1$ is hydrogen or a suitable substituent; and $R^2$ is hydrogen or halogen, or a salt thereof.

The object compound (I) and a salt thereof of the present invention can be prepared by the following processes.

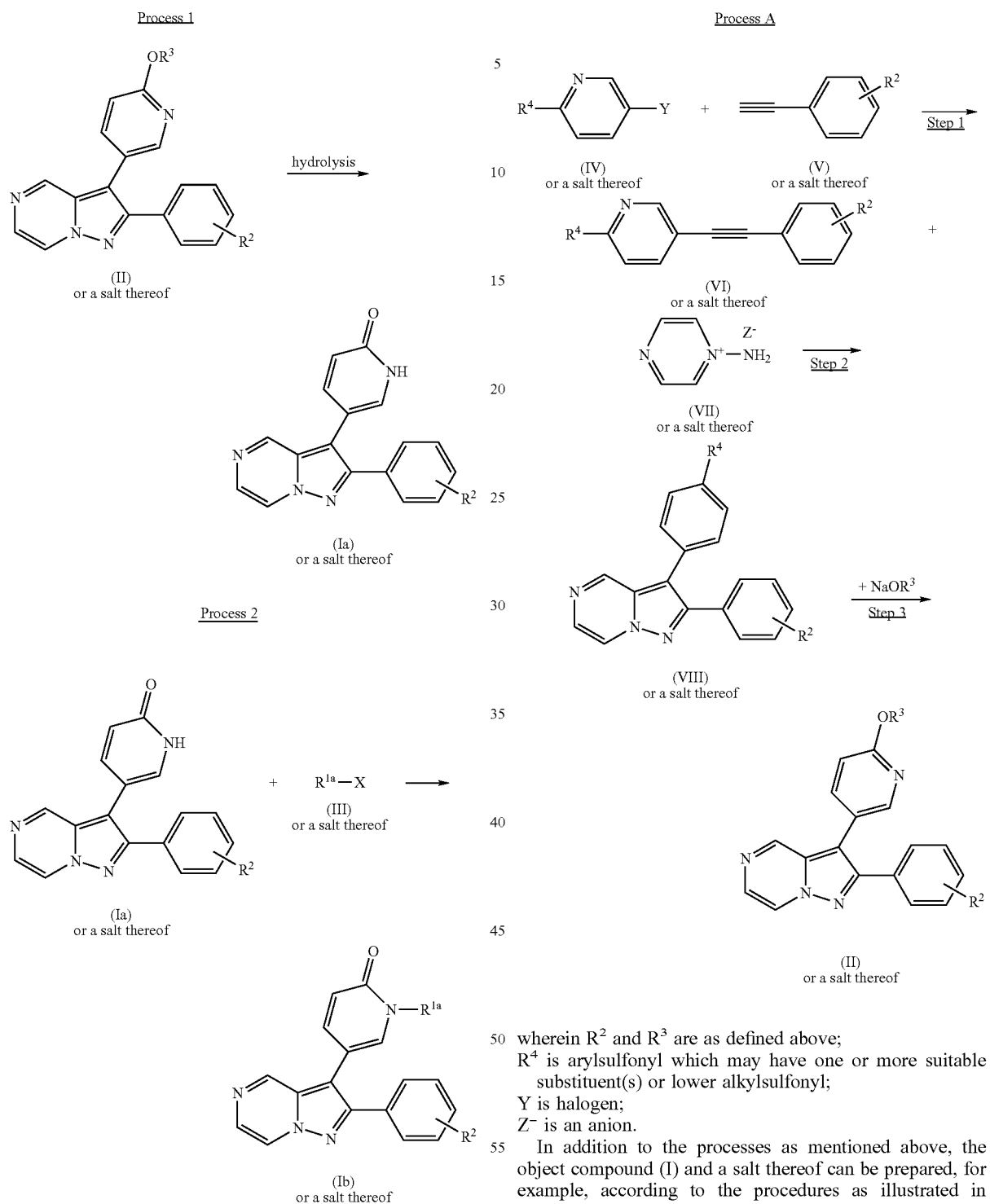

wherein $R^2$ and $R^3$ are as defined above;
$R^4$ is arylsulfonyl which may have one or more suitable substituent(s) or lower alkylsulfonyl;
Y is halogen;
$Z^-$ is an anion.

In addition to the processes as mentioned above, the object compound (I) and a salt thereof can be prepared, for example, according to the procedures as illustrated in Examples in the present specification or in a manner similar thereto.

The starting compounds can be prepared, for example, according to the procedures as illustrated in Preparations in the present specification or in a manner similar thereto.

The object compound (I) and a salt thereof can be prepared according to the methods as shown in Preparations or Examples, or in a manner similar thereto.

It is to be noted that the object compound (I) may include the geometrical isomer(s) due to the double bond(s) and/or wherein $R^2$ is as defined above,
$R^{1a}$ is a suitable substituent;
$R^3$ is lower alkyl; and
X is a leaving group.

The starting compound(II) or a salt thereof is novel and can be prepared, for example, by the following reaction schemes.

the stereo isomer(s) due to the asymmetric carbon atom(s). In this regard, one isomer can be converted to another according to a conventional method in this field of the art.

It is also to be noted that the solvating form of the compound (I) (e.g. hydrate, etc.) and any form of the crystal of the compound (I) are included within the scope of the present invention.

Suitable salts of the object compound (I) are conventional pharmaceutically acceptable ones and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, trifluoroacetate, maleate, tartrate, fumarate, methanesulfonate, benzenesulfonate, formate, toluenesulfonate, etc.), an inorganic acid salt (e.g. hydrochloride, hydrobromide, hydriodide, sulfate, phosphate, etc.), a salt with an amino acid (e.g. arginine, aspartic acid, glutamic acid, etc.), and the like.

Suitable examples and illustrations of the various definitions which the present invention includes within the scope thereof and which appear in the above and following description in the present specification are explained in detail as follows.

Suitable example of "substituent" for $R^1$ is selected from the group consisting of lower alkyl, ar(lower)alkyl or cyclo(lower)alkyl which may be interrupted by an oxygen atom.

The term "lower" is intended to mean 1 to 6 carbon atom(s) unless otherwise indicated.

Suitable "lower alkyl" may include straight or branched ones such as methyl, ethyl, propyl, isopropyl, butyl, tert-butyl, pentyl, hexyl or the like, in which the preferred one may be (C1–C4)alkyl and the more preferred one may be methyl, ethyl, propyl or isopropyl.

Suitable "cyclo(lower)alkyl" may be cyclo(C3–C8)-alkyl such ascyclopropyl, cyclobutyl, cyclopentyl, cyclohexyl, cycloheptyl, cyclooctyl or the like, in which the preferred one may be cyclo(C5–C7) alkyl such as cyclopentyl, cyclohexyl orcycloheptyl.

Said "cyclo(lower)alkyl" maybe interrupted by an oxygen atom, in which the preferred one may be saturated 3–8-membered heteromonocyclic group containing an oxygen atom such as tetrahydrofuranyl or tetrahydropyranyl.

Suitable "ar(lower)alkyl" may include phenyl(lower)alkyl (e.g. benzyl, phenethyl, etc.), diphenyl (lower)alkyl (e.g. benzhydryl, etc.), triphenyl(lower)alkyl (e.g. trityl, etc.), naphthyl(lower)alkyl, indenyl(lower)alkyl or anthryl (lower)alkyl and the like, in which the preferred one may be phenyl(lower)alkyl, and the more preferred one may be phenyl(C1–C4)alkyl.

Suitable "halogen" may include fluoro, chloro, bromo and iodo.

Suitable "a leaving group" may include halogen as mentioned above, hydroxy, acyloxy such as alkanoyloxy (e.g. acetoxy, propionyloxy, etc.),sulfonyloxy (e.g. mesyloxy, tosyloxy, etc.), and the like.

Suitable "anion" may be formate, acetate, trifluoroacetate, maleate, tartrate, methanesulfonate, benzenesulfonate, toluenesulfonate, chloride, bromide, iodide, sulfate, phosphate, or the like.

Suitable "arylsulfonyl" may include phenylsulfonyl, tolylsulfonyl, naphthylsulfonyl and the like, and said "arylsulfonyl" may have one or more (preferably 1 to 3) suitable substituent(s) such as lower alkoxy (e.g. methoxy, ethoxy, propoxy, isopropoxy, butoxy, tert-butoxy, pentyloxy, hexyloxy, etc.), aforesaid halogen, or the like.

Suitable "lower alkylsulfonyl" may include methylsulfonyl, ethylsulfonyl, propylsulfonyl, isopropylsulfonyl, butylsulfonyl, tert-butylsulfonyl and the like, in which the preferred one may be methylsulfonyl.

The processes for preparing the object pyrazolopyrazine compound(I) are explained in detail in the following.

Process 1

The compound (Ia) or a salt thereof can be prepared by subjecting the compound (II) or a salt thereof to hydrolysis.

Suitable salt of the compound (II) can be referred to an acid addition salt as exemplified for the compound (I).

This reaction is carried out in accordance with a conventional method.

The hydrolysis is preferably carried out in the presence of a base or an acid including Lewis acid.

Suitable base includes an inorganic base and an organic base such as an alkali metal (e.g. sodium, potassium, etc.), an alkaline earth metal (e.g. magnesium, calcium, etc.), the hydroxide or carbonate or hydrogencarbonate thereof, trialkylamide (e.g. trimethylamine, triethylamine, etc.), hydrazine, picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid includes an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, hydrogen chloride, hydrogen bromide, etc.).

The elimination using Lewis acid such as $BBr_3$, $BCl_3$, $BF_3$, $AlCl_3$, $TiCl_4$ or the like is preferably carried out in the presence of cation trapping agents (e.g. anisole, phenol, etc.).

The reaction is usually carried out in a solvent such as water, an alcohol (e.g. methanol, ethanol, isopropyl alcohol, etc.), tetrahydrofuran, dioxane, toluene, methylene chloride, ethylene dichloride, chloroform, N,N-dimethylformamide, N,N-dimethylacetamide, or any other organic solvents which do not adversely affect the reaction, or a mixture thereof.

A liquid base or acid can be also used as the solvent. The reaction temperature is not critical and the reaction is usually carried out under cooling to heating.

Process 2

The compound (Ib) or a salt thereof can be prepared by reacting the compound (Ia) or a salt thereof with the compound (III) or a salt thereof.

Suitable salt of the compound (Ia) can be referred to an acid addition salt as exemplified for the compound (I).

Suitable salt of the compound (III) can be referred to the ones as exemplified for the compound (I).

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, sec-butanol, amyl alcohol, diethyl ether, dioxane, tetrahydrofuran, dimethyl sulfoxide, or any other organic solvent which does not adversely affect the reaction, preferably in ones having strong polarities. Among the solvents, hydrophilic solvents may be used in a mixture with water. When the compound (III) is in liquid, it can also be used as a solvent. The reaction is preferably conducted in the presence of a base, for example, inorganic base such as alkali metal hydroxide (e.g. sodium hydroxide, potassium hydroxide, etc.), alkali metal carbonate, alkali metal bicarbonate, alkali metal hydride (e.g. sodium hydride), alkali metal alkoxide (e.g. EtONa, t-BuOK, etc.) organic base such as trialkylamine, and the like.

The reaction temperature is not critical, and the reaction is usually carried out at ambient temperature, under warming or under heating.

The present reaction is preferably carried out in the presence of alkali metal halide (e.g. sodium iodide, potassium iodide, etc.), alkali metal thiocyanate (e.g. sodium thiocyanate, potassium thiocyanate, etc.), di(lower)alkyl azodicarboxylate (e.g. diethyl azodicarboxylate, diisopropyl azodicarboxylate, etc.) or the like.

When X is —OH, activation of OH with triphenylphosphine and the like may be necessary.

Process A

Step 1

The reaction of this step can be carried out by the method disclosed in Preparation 3 mentioned later or the similar manners thereto.

Step 2

The compound (VIII) or a salt thereof can be prepared by reacting the compound. (VI) or a salt thereof with the compound (VII) or a salt thereof.

Suitable salts of the compounds (VI), (VII) and (VIII) can be referred to acid addition salts as exemplified for the compound (I).

The reaction is usually carried out in a solvent such as water, methylene chloride, ethylene chloride, N,N-dimethylformamide or any other solvent which does not adversely influence the reaction or a mixture thereof.

The reaction can be carried out in the presence of a base such as alkali metal hydroxide (e.g. sodium hydroxide, potassium hydroxide, etc.), alkalimetal carbonate, alkalimetal bicarbonate, alkali metal hydride (e.g. sodium hydride), alkali metal alkoxide (e.g. EtONa, t-BuOK, etc.) organic base such as trialkylamine, ar(lower)alkyltri(lower) alkylammonium halide (e.g. benzyltrimethylammonium chloride, etc.) or the like.

The reaction temperature is not critical and the reaction is usually carried out under cooling, at room temperature or under warming.

Step 3

The reaction of this step can be carried out by the method disclosed in Preparation 5 mentioned later or the similar manners thereto.

The object compound (I) of the present invention is anadenosine antagonist and possesses the various pharmacological actions as stated before.

In order to show the usefulness of the compound (I) of the present invention, the pharmacological test result of the representative compound of the present invention is shown in the following.

Test 1: Adenosine Antagonistic Activity

[I] Test Method

The adenosine antagonistic activity [Ki(nM)] of the test compound was examined by radioligand binding techniques using 8-cyclopentyl-1,3-dipropylxanthine, [dipropyl-2,3-$^3$H (N)] ([$^3$H]DPCPX, 4.5 nM) for human $A_1$ receptor and [$^3$H]CGS 21680 (20 nM) for human $A_{2a}$ receptor.

[II] Test Compound 3-(2(1H)-Pyridinon-5-yl)-2-phenylpyrazolo[1,5-a]pyrazine (Example 1)

3- (1-Methyl-2 (1H)-pyridinon-5-yl)-2-phenylpyrazolo[1,5-a]pyrazine (Example 2)

3-(1-Ethyl-2(1H)-pyridinon-5-yl)-2-(4-fluorophenyl) pyrazolo[1,5-a]pyrazine (Example 9)

[III] Test Result

TABLE 1

| Test compound | Adenosine receptor binding (Ki:nM) | |
|---|---|---|
| (Example No.) | $A_1$ | $A_{2a}$ |
| 1 | 0.18 | 0.68 |
| 2 | 0.35 | 3.28 |
| 9 | 0.36 | 4.44 |

Test 2: Anticatalepsy Activity in Mouse

[I] Test Method

The test compound (3.2 mg/kg) was administered orally with ddY mice (n=7). Then, haloperidol (0.32 mg/kg) was injected intraperitoneally 30 min. after the administration of the compound. Thirty min. after the injection, the cataleptic responses of mice were measured. The forelimbs of each mouse were placed on a 3 cm high, 3 mm wide horizontal bar, and the duration of cataleptic posture was measured for up to 30 sec.

[II] Test Compound 3-(2(1H)-Pyridinon-5-yl)-2-phenylpyrazolo[1,5-a]pyrazine (Example 1)

3- (1-Methyl-2(1H)-pyridinon-5-yl)-2-phenylpyrazolo[1, 5-a]pyrazine (Example 2)

3-(1-Ethyl-2(1H)-pyridinon-5-yl)-2-(4-fluorophenyl) pyrazolo[1,5-a]pyrazine (Example 9)

[III] Test Result

TABLE 2

| Test compound (Example No.) | Manifestation rate of catalepsy (number of mouse) |
|---|---|
| 1 | 1/7 |
| 2 | 0/7 |
| 9 | 0/7 |

The pyrazolopyrazine compound (I) and a salt thereof of this invention are useful as adenosine antagonists (especially, $A_1$ receptor and $A_2$ (particularly $A_{2a}$) receptor dual antagonists) and for the prevention and/or the treatment of depression, dementia (e.g. Alzheimer's disease, cerebrovascular dementia, dementia accompanying Parkinson's disease, etc.), Parkinson's disease, anxiety, pain, cerebrovascular disease, heart failure, hypertension, circulatory insufficiency, post-resuscitation, asystole, bradyarrhythmia, electro-mechanical dissociation, hemodynamic collapse, SIRS (systemic inflammatory response syndrome), multiple organ failure, renal failure (renal insufficiency), renal toxicity, nephrosis, nephritis, edema, obesity, bronchial asthma, gout, hyperuricemia, sudden infant death syndrome, immunosuppression, diabetes, ulcer, pancreatitis, Meniere's syndrome, anemia, dialysis-induced hypotension, constipation, ischemic bowel disease, ileus, myocardial infarction, thrombosis, obstruction, arteriosclerosis obliterans, thrombophlebitis, cerebral infarction, transient ischemic attack, angina pectoris, and the like.

The pharmaceutical composition of this invention can be used in the form of a pharmaceutical preparation, for example, in a solid, semisolid or liquid form, which contains the pyrazolo-pyrazine compound (I) or a pharmaceutically acceptable salt thereof as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. In addition, auxiliary, stabilizing agents, thickening agents, coloring agents and perfumes may be used where necessary. The pyrazolopyrazine compound (I) or a pharmaceutically acceptable salt thereof is included in a pharmaceutical composition in an amount sufficient to produce the desired aforesaid pharmaceutical effect upon the process or condition of diseases.

For applying the composition to a human being or an animal, it is preferable to apply it by intravenous, intramuscular, pulmonary or oral administration, or insufflation. While the dosage of therapeutically effective amount of the pyrazolo-pyrazine compound (I) varies depending on the age and condition of each individual patient to be treated, in the case of intravenous administration, a daily dose of 0.01–100 mg of the pyrazolo-pyrazine compound (I) per kg weight of a human being or an animal, in the case of intramuscular administration, a daily dose of 0.1–100 mg of the pyrazolopyrazine compound (I) per kg weight of a human being or an animal, and in case of oral administration, a daily dose of 0.5–100 mg of the pyrazolopyrazine compound (I) per kg weight of a human being or an animal is generally given for the prevention and/or treatment of the aforesaid diseases.

The following Preparations and Examples are given for the purpose of illustrating the present invention in more detail.

Preparation 1

To a solution of 2,5-dibromopyridine (12.0 g) and thiophenol (5.46 mL) in DME (50 mL) was added sodium tert-butoxide (5.35 g) at room temperature and the mixture was stirred at 100° C. for 15 h. The reaction mixture was poured into brine, extracted with EtOAc, washed with brine, dried over sodium sulfate, evaporated in vacuo. The residue was purified by silica gel column chromatography (n-hexane-EtOAc 30:1) to give 5-bromo-2-(phenylsulfanyl)pyridine (13.69 g) as an oil.

IR (neat) 3055, 1554, 1475, 1441, 1352 cm$^{-1}$
$^1$H NMR (DMSO-d$_6$) δ 6.92 (1H, dd, J=8.6, 0.5 Hz), 7.45–7.65 (5H, m), 7.89 (1H, dd, J=8.6, 2.5 Hz), 8.54 (1H, d, J=2.5 Hz)
APCI-MS m/z 266, 268 (MH$^+$)

Preparation 2

To a solution of 5-bromo-2-(phenylsulfanyl)pyridine (12.9 g) in CH$_2$Cl$_2$ (500 mL) was added 70% mCPBA (24.0 g) at 5° C. and the mixture was stirred at room temperature for 4.5 h. The reaction mixture was concentrated in vacuo, diluted with EtOAc, washed with a mixture of 10% Na$_2$S$_2$O$_3$ and saturated sodium hydrogen carbonate, water, and brine, dried over sodium sulfate, evaporated in vacuo to give 5-bromo-2-(phenylsulfonyl)pyridine (13.7 g) as a crystaline solid.

IR (KBr) 3107, 3059, 1579, 1562, 1545, 1442, 1356, 1327 cm$^{-1}$
$^1$H NMR (DMSO-d$_6$) δ 7.58–7.82 (3H, m), 7.93–8.02 (2H, m), 8.16 (1H, dd, J=8.4, 0.6 Hz), 8.42 (1H, dd, J=8.4, 2.3 Hz), 8.87 (1H, dd, J=2.3, 0.6 Hz)
APCI-MS m/z 298, 300 (MH$^+$)

Preparation 3

To a mixture of 5-bromo-2-(phenylsulfonyl)pyridine (6.00 g), ethynylbenzene (2.87 mL), dichlorobis(triphenylphosphine)palladium (II) (140 mg) and CuI (38 mg) in DMF (90 mL) was added triethylamine (8.42 mL) and the mixture was stirred at 60° C. for 1 h. The reaction mixture was diluted with EtOAc, washed with water and brine, dried over sodium sulfate, evaporated in vacuo. The residue was purified by silica gel column chromatography (CHCl$_3$ to CHCl$_3$-EtOAc 10:1) to give 5-(phenylethynyl)-2-(phenylsulfonyl)pyridine (6.33 g) as a solid.

IR (KBr) 3057, 2220, 1568, 1487, 1446, 1362, 1333 cm$^{-1}$
$^1$H NMR (DMSO-d$_6$) δ 7.40–7.83 (5H, m), 7.95–8.05 (2H, m), 8.23–8.36 (2H, m), 8.87 (1H, dd, J=1.9, 0.9 Hz)
APCI-MS m/z 320 (MH$^+$)

Preparation 4

To a mixture of 5-(phenylethynyl)-2-(phenylsulfonyl)pyridine (6.00 g) and K$_2$CO$_3$ (13.0 g) in DMF (120 mL) was added 1-aminopyrazin-1-ium iodide (12.6 g) and the mixture was stirred at room temperature for 1 h, then stirred at 60° C. for 8 h. To the reaction mixture was added K$_2$CO$_3$ (7.80 g) and 1-aminopyrazin-1-ium iodide (8.38 g) and stirred at room temperature for 1 h, then stirred at 60° C. for 12 h. To the reaction mixture was added further K$_2$CO$_3$ (7.80 g) and 1-aminopyrazin-1-ium iodide (8.38 g) and stirred at room temperature for 1 h, then stirred at 60° C. for 26 h. The mixture was poured into ice water and extracted with EtOAc, washed with water and brine, dried over sodium sulfate, evaporated in vacuo. The residue was purified by silica gel column chromatography (n-hexane-EtOAc 3:1 to CHCl$_3$-MeOH 20:1) to give 2-phenyl-3-[6-(phenylsulfonyl)-3-pyridinyl]pyrazolo[1,5-a]pyrazine (4.14 g) as an amorphous solid.

IR (KBr) 1581, 1522, 1446, 1315 cm$^{-1}$
$^1$H NMR (DMSO-d$_6$) δ 7.30–7.55 (5H, m), 7.55–7.83 (3H, m), 7.90–8.20 (3H, m), 8.20–8.32 (2H, m), 8.67–8.75 (1H, m), 8.92 (1H, dd, J=4.8, 1.4 Hz), 9.23 (1H, d, J=1.4 Hz)
APCI-MS m/z 413 (MH$^+$)

Preparation 5

A mixture of 2-phenyl-3-[6-(phenylsulfonyl)-3-pyridinyl]pyrazolo[1,5-a]pyrazine (3.93 g) and sodium methoxide (5.2M MeOH solution, 10 mL) in MeOH (60 mL) and 1,4-dioxane (60 mL) was stirred at 85° C. for 1 h. The reaction mixture was concentrated in vacuo, and ice water was added, extracted, with EtOAc, washed with water and brine, dried over sodium sulfate, evaporated in vacuo. The residue was purified by silica gel column chromatography (n-hexane-EtOAc 2:3) to give 3-(6-methoxy-3-pyridinyl)-2-phenylpyrazolo[1,5-a]pyrazine (2.37 g) as an oil.

IR (neat) 3049, 2945, 1606, 1535, 1498, 1481, 1462, 1369 cm$^{-1}$
$^1$H NMR (DMSO-d$_6$) δ 3.91 (3H, s), 6.92 (1H, d, J=8.5 Hz), 7.35–7.60 (5H, m), 7.72 (1H, dd, J=8.5, 2.4 Hz), 7.99 (1H, d, J=4.9 Hz), 8.26 (1H, d, J=2.4 Hz), 8.86 (1H, dd, J=4.9, 1.4 Hz), 9.06 (1H, d, J=1.4 Hz)
APCI-MS m/z 303 (MH$^+$)

Preparation 6

5-[(4-Fluorophenyl)ethynyl]-2-(phenylsulfonyl)pyridine was obtained in a similar manner to that of Preparation 3.

IR (KBr) 3062, 2222, 2599, 1568, 1508, 1446, 1321 cm$^{-1}$
$^1$H NMR (DMSO-d$_6$) δ 7.25–7.40 (2H, m), 7.58–7.80 (5H, m), 7.92–8.05 (2H, m), 8.20–8.35 (2H, m), 8.86 (1H, dd, J=1.8, 0.9 Hz)
APCI-MS m/z 338 (MH$^+$)

Preparation 7

2-(4-Fluorophenyl)-3-[6-(phenylsulfonyl)-3-pyridinyl]pyrazolo[1,5-a]pyrazine was obtained in a similar manner to that of Preparation 4.

IR (KBr) 3051, 1602, 1583, 1525, 1466, 1444, 1319 cm$^{-1}$
$^1$H NMR (DMSO-d$_6$) δ 7.20–7.35 (2H, m), 7.45–7.58 (2H, m), 7.60–7.80 (3H, m), 7.95–8.10 (3H, m), 8.10–8.29 (2H, m), 8.71–8.78 (1H, m), 8.91 (1H, dd, J=4.7, 1.4 Hz), 9.23 (1H, d, J=1.4 Hz)
APCI-MS m/z 431 (MH$^+$)

Preparation 8

2-(4-Fluorophenyl)-3-(6-methoxy-3-pyridinyl)pyrazolo[1,5-a]pyrazine-was obtained in a similar manner to that of Preparation 5.

IR (KBr) 3095, 3016, 1606, 1533, 1498, 1462, 1367 cm$^{-1}$
$^1$H NMR (DMSO-d$_6$) δ 3.91 (3H, s), 6.93 (1H, dd, J=8.6, 0.6 Hz), 7.20–7.35 (2H, m), 7.53–7.65 (2H, m), 7.72 (1H, dd, J=8.6, 2.5 Hz), 8.00 (1H, d, J=4.7 Hz), 8.27 (1H, d, J=2.5 Hz), 8.86 (1H, dd, J=4.7, 1.4 Hz), 9.06 (1H, d, J=1.4 Hz)
APCI-MS m/z 321 (MH$^+$)

Preparation 9

5-[(2-Fluorophenyl)ethynyl]-2-(phenylsulfonyl)pyridine was obtained in a similar manner to that of Preparation 3.

IR (KBr) 2225, 1572, 1493, 1444, 1323 cm$^{-1}$
$^1$H NMR (DMSO-d$_6$) δ 7.25–7.47 (2H, m), 7.47–7.82 (5H, m), 7.94–8.06 (2H, m), 8.26 (1H, dd, J=8.1, 0.8 Hz), 8.34 (1H, dd, J=8.1, 2.0 Hz), 8.88 (1H, dd, J=2.0, 0.8 Hz)
APCI-MS m/z 338 (MH$^+$)

Preparation 10

2-(2-Fluorophenyl)-3-[6-(phenylsulfonyl)-3-pyridinyl]pyrazolo[1,5-a]pyrazine was obtained in a similar manner to that of Preparation 4.

IR (KBr) 3093, 1585, 1531, 1469, 1448, 1317 cm$^{-1}$
$^1$H NMR (DMSO-d$_6$) δ 7.21–7.41 (2H, m), 7.47–7.81 (5H, m), 7.95–8.05 (2H, m), 8.05–8.27 (3H, m), 8.69 (1H, d, J=1.5 Hz), 8.95 (1H, dd, J=4.7, 1.4 Hz), 9.35 (1H, d, J=1.4 Hz)
APCI-MS m/z 431 (MH$^+$)

Preparation 11

2-(2-Fluorophenyl)-3-(6-methoxy-3-pyridinyl)pyrazolo[1,5-a]pyrazine was obtained in a similar manner to that of Preparation 5.

$^1$H NMR (DMSO-d$_6$) δ 3.87 (3H, s), 6.86 (1H, dd, J=8.5, 0.4 Hz), 7.20–7.40 (2H, m), 7.45–7.71 (3H, m), 8.03 (1H, d, J=4.8 Hz), 8.18 (1H, d, J=1.9 Hz), 8.89 (1H, dd, J=4.8, 1.4 Hz), 9.20 (1H, d, J=1.4 Hz)
ESI-MS m/z 321 (MH$^+$)

EXAMPLE 1

A mixture of 3-(6-methoxy-3-pyridinyl)-2-phenylpyrazolo[1,5-a]pyrazine (2.36 g) and concd. HCl (7.8 mL) in 1,4-dioxane (48 mL) was stirred at 100° C. for 1 h. After cooling to room temperature, to the reaction mixture was added 5N sodium hydroxide solution and adjusted to pH 8, extracted with EtOAc, washed with brine, dried over sodium sulfate, evaporated in vacuo. The resulting solid was collected by filtration and washed with ether to give 3-(2(1H)-pyridinon-5-yl)-2-phenylpyrazolo[1,5-a]pyrazine (1.95 g) as a solid.

mp: >250° C.
IR (KBr) 1664, 1631, 1549, 1464, 1335, 1252 cm$^{-1}$
$^1$H NMR (DMSO-d$_6$) δ 6.40 (1H, d, J=9.4 Hz), 7.34 (1H, dd, J=9.4, 2.6 Hz), 7.39–7.53 (3H, m), 7.55 (1H, d, J=2.6 Hz), 7.60–7.72 (2H, m), 7.96 (1H, d, J=4.7 Hz), 8.82 (1H, dd, J=4.7, 1.4 Hz), 9.08 (1H, d, J=1.4 Hz), 11.84 (1H, br s)
APCI-MS m/z 289 (MH$^+$)

EXAMPLE 2

To a suspension of 3-(2(1H)-pyridinon-5-yl)-2-phenylpyrazolo[1,5-a]pyrazine (120 mg) in DMF (3 mL) was added NaH (60% oil suspension, 25 mg) at room temperature and the mixture was stirred at the same temperature for 10 min. To the mixture was added iodomethane (0.039 mL). After stirring at room temperature for 15 h, the reaction mixture was poured into 10% NaCl solution, extracted with EtOAc, washed with 10% NaCl solution and brine, dried over sodium sulfate, evaporated in vacuo. The residue was purified by silica gel column chromatography (EtOAc to CH$_2$Cl$_2$-MeOH 10:1) to give 3-(1-methyl-2(1H)-pyridinon-5-yl)-2-phenylpyrazolo[1,5-a]pyrazine (114.5 mg) as a solid.

mp: 168–169° C. (CH$_2$Cl$_2$-hexane)
IR (KBr) 3030, 1662, 1595, 1523, 1468 cm$^{-1}$
$^1$H NMR (CDCl$_3$) δ 3.60 (3H, s), 6.66 (1H, d, J=9.4 Hz), 7.32 (1H, dd, J=9.4, 2.6 Hz), 7.35–7.48 (4H, m), 7.60–7.75 (2H, m), 7.93 (1H, d, J=4.8 Hz), 8.40 (1H, dd, J=4.8, 1.4 Hz), 8.98 (1H, d, J=1.4 Hz)
APCI-MS m/z 303 (MH$^+$)

EXAMPLE 3

3-(1-Isopropyl-2(1H)-pyridinon-5-yl)-2-phenylpyrazolo[1,5-a]pyrazine was obtained in a similar manner to that of Example 2.

mp: 196–197° C. (CH$_2$Cl$_2$-hexane)
IR (KBr) 2976, 1658, 1593, 1516, 1466 cm$^{-1}$
$^1$H NMR (CDCl$_3$) δ 1.26 (6H, d, J=6.8 Hz), 5.31 (1H, hept, J=6.8 Hz), 6.67 (1H, dd, J=9.1, 0.6 Hz), 7.27–7.49 (5H,m), 7.57–7.72 (2H, m), 7.93 (1H, d, J=4.7 Hz), 8.40 (1H, dd, J=4.7, 1.4 Hz), 8.99 (1H, d, J=1.4 Hz)
APCI-MS m/z 331 (MH$^+$)

EXAMPLE 4

3-(1-Ethyl-2(1H)-pyridinon-5-yl)-2-phenylpyrazolo[1,5-a]pyrazine was obtained in a similar manner to that of Example 2.

mp 192–193° C. (EtOAc)
IR (KBr) 3041, 2993, 1666, 1593, 1527 cm$^{-1}$
$^1$H NMR (CDCl$_3$) δ 1.35 (3H, t, J=7.2 Hz), 4.01 (2H, q, J=7.2 Hz), 6.66 (1H, d, J=10.1 Hz), 7.30–7.50 (5H, m), 7.60–7.75 (2H, m), 7.93 (1H, d, J=4.7 Hz), 8.40 (1H, dd, J=4.7, 1.4 Hz), 8.99 (1H, d, J=1.4 Hz)
APCI-MS m/z 317 (MH$^+$)

EXAMPLE 5

3-(1-n-Propyl-2(1H)-pyridinon-5-yl)-2-phenylpyrazolo[1,5-a]pyrazine was obtained in a similar manner to that of Example 2.

mp: 165–166° C. (CH$_2$Cl$_2$-hexane)
IR (KBr) 3030, 2962, 2871, 1660, 1599, 1522, 1466, 1437 cm$^{-1}$
$^1$H NMR (CDCl$_3$) δ 0.95 (3H, t, J=7.4 Hz), 1.65–1.90 (2H, m), 3.92 (2H, t, J=7.3 Hz), 6.66 (1H, d, J=10.3 Hz), 7.26–7.55 (5H, m), 7.57–7.75 (2H, m), 7.93 (1H, d, J=4.8 Hz), 8.40 (1H, dd, J=4.8, 1.1 Hz), 8.98 (1H, d, J=1.1 Hz)
APCI-MS m/z 331 (MH$^+$)

EXAMPLE 6

3-(2(1H)-Pyridinon-5-yl)-2-(4-fluorophenyl)pyrazolo[1,5-a]pyrazine was obtained in a similar manner to that of Example 1.

IR (KBr) 1660, 1620, 1529, 1493 cm$^{-1}$
$^1$H NMR (DMSO-d$_6$) δ 6.41 (1H, d, J=9.1 Hz), 7.25–7.40 (3H, m), 7.56 (1H, d, J=2.2 Hz), 7.60–7.75 (2H, m), 7.97 (1H, d, J=4.8 Hz), 8.81 (1H, dd, J=4.8, 1.4 Hz), 9.07 (1H, d, J=1.4 Hz), 11.84 (1H, br s)
APCI-MS m/z 307 (MH$^+$)

EXAMPLE 7

3-(1-Methyl-2(1H)-pyridinon-5-yl)-2-(4-fluorophenyl)pyrazolo[1,5-a]pyrazine was obtained in a similar manner to that of Example 2.

mp: 222–223° C. (EtOAc)

IR (KBr) 3093, 1678, 1622, 1601, 1535, 1466 cm$^{-1}$
$^1$H NMR (CDCl$_3$) δ 3.60 (3H, s), 6.67 (1H, d, J=9.3 Hz), 7.05–7.17 (2H, m), 7.30 (1H, dd, J=9.3, 2.5 Hz), 7.39 (1H, d, J=2.5 Hz), 7.60–7.72 (2H, m), 7.94 (1H, d, J=4.7 Hz), 8.38 (1H, dd, J=4.7, 1.4 Hz), 8.97 (1H, d, J=1.4 Hz)
APCI-MS m/z 321 (MH$^+$)

EXAMPLE 8

3-(1-Isopropyl-2(1H)-pyridinon-5-yl)-2-(4-fluorophenyl)pyrazolo[1,5-a]pyrazine was obtained in a similar manner to that of Example 2.
mp: 214–215° C. (EtOAc)
IR (KBr) 2985, 1658, 1595, 1527, 1516 cm$^{-1}$
$^1$H NMR (CDCl$_3$) δ 1.29 (6H, d, J=6.8 Hz), 5.32 (1H, hept, J= 6.8 Hz), 6.68 (1H, d, J=10.0 Hz), 7.05–7.18 (2H, m), 7.28–7.38 (2H, m), 7.59–7.70 (2H, m), 7.94 (1H, d, J=4.7 Hz), 8.39 (1H, dd, J=4.7, 1.4 Hz), 8.98 (1H, d, J=1.4 Hz)
APCI-MS m/z 349 (MH$^+$)

EXAMPLE 9

3-(1-Ethyl-2(1H)-pyridinon-5-yl)-2-(4-fluorophenyl)pyrazolo[1,5-a]pyrazine was obtained in a similar manner to that of Example 2.
mp: 165–166° C. (EtOAc)
IR (KBr) 1662, 1601, 1529, 1469, 1329 cm$^{-1}$
$^1$H NMR (CDCl$_3$) δ 1.37 (3H, t, J=7.2 Hz), 4.02 (2H, q, J=7.2 Hz), 6.67 (1H, d, J=10.0 Hz), 7.05–7.18 (2H, m), 7.26–7.38 (2H, m), 7.60–7.73 (2H, m), 7.94 (1H, d, J=4.7 Hz), 8.39 (1H, dd, J=4.7, 1.4 Hz), 8.98 (1H, d, J=1.4 Hz)
APCI-MS m/z 335 (MH$^+$)

EXAMPLE 10

3-(1-n-Propyl-2(1H)-pyridinon-5-yl)-2-(4-fluorophenyl)pyrazolo[1,5-a]pyrazine was obtained in a similar manner to that of Example 2.
mp 183–184° C. (EtOAc)
IR (KBr) 1670, 1602, 1525, 1493, 1468 cm$^{-1}$
$^1$H NMR(CDCl$_3$) δ 0.96 (3H, t, J=7.4 Hz), 1.66–1.90 (2H, m), 3.93 (2H, t, J=7.3 Hz), 6.67 (1H, d, J=10.2 Hz), 7.03–7.18 (2H, m), 7.22–7.37 (2H, m), 7.58–7.73 (2H, m), 7.93 (1H, d, J=4.7 Hz), 8.38 (1H, dd, J=4.7, 1.4 Hz), 8.97 (1H, d, J=1.4 Hz)
APCI-MS m/z 349 (MH$^+$)

EXAMPLE 11

3-(2(1H)-Pyridinon-5-yl)-2-(2-fluorophenyl)pyrazolo[1,5-a]pyrazine was obtained in a similar manner to that of Example 1.
IR (KBr) 1658, 1622, 1549, 1468, 1435 cm$^{-1}$
$^1$H NMR (DMSO-d$_6$) δ 6.34 (1H, d, J=9.3 Hz), 7.25–7.65 (6H, m), 8.00 (1H, d, J=4.8 Hz), 8.84 (1H, dd, J=4.8, 1.4 Hz), 9.18 (1H, d, J=1.4 Hz), 11.74 (1H, br s)
APCI-MS m/z 307 (MH$^+$)

EXAMPLE 12

3-(1-Methyl-2(1H)-pyridinon-5-yl)-2-(2-fluorophenyl)pyrazolo[1,5-a]pyrazine was obtained in a similar manner to that of Example 2.
mp: 193–194° C. (EtOAc)
IR (KBr) 1670, 1597, 1531, 1514, 1468 cm$^{-1}$
$^1$H NMR (CDCl$_3$) δ 3.55 (3H, s), 6.60 (1H, d, J=9.1 Hz), 7.07–7.37 (4H, m), 7.37–7.60 (2H, m), 7.96 (1H, d, J=4.8 Hz), 8.42 (1H, dd, J=4.8, 1.4 Hz), 9.06 (1H, d, J=1.4 Hz)
APCI-MS m/z 321 (MH$^+$)

EXAMPLE 13

3-(1-Isopropyl-2(1H)-pyridinon-5-yl)-2-(2-fluorophenyl)pyrazolo[1,5-a]pyrazine was obtained in a similar manner to that of Example 2.
mp: 150–151° C. (EtOAc-Et$_2$O)
IR (KBr) 2978, 1660, 1593, 1518, 1468, 1446 cm$^{-1}$
$^1$H NMR (CDCl$_3$) δ 1.19 (6H, d, J=6.8 Hz), 5.27 (1H, hept, J=6.8 Hz), 6.63 (1H, dd, J=9.3, 0.4 Hz), 7.07–7.60 (6H, m), 7.96 (1H, d, J=4.8 Hz), 8.42 (1H, dd, J=4.8, 1.4 Hz), 9.07 (1H, d, J=1.4 Hz)
APCI-MS m/z 349 (MH$^+$)

EXAMPLE 14

3-(1-Ethyl-2(1H)-pyridinon-5-yl)-2-(2-fluorophenyl)pyrazolo[1,5-a]pyrazine was obtained in a similar manner to that of Example 2.
mp: 173–174° C. (EtOAc)
IR (KBr) 1666, 1597, 1531, 1468 cm$^{-1}$
$^1$H NMR (CDCl$_3$) δ 1.29 (3H, t, J=7.2 Hz), 3.96 (2H, q, J=7.2 Hz), 6.61 (1H, dd, J=9.3, 0.5 Hz), 7.07–7.36 (4H, m), 7.36–7.60 (2H, m), 7.96 (1H, d, J=4.8 Hz), 8.42 (1H, dd, J=4.8, 1.4 Hz), 9.06 (1H, d, J=1.4 Hz)
APCI-MS m/z 335 (MH$^+$)

EXAMPLE 15

3-(1-n-Propyl-2(1H)-pyridinon-5-yl)-2-(2-fluorophenyl)pyrazolo[1,5-a]pyrazine was obtained in a similar manner to that of Example 2.
mp: 127–128° C. (EtOAc-Et$_2$O)
IR (KBr) 2972, 2921, 1662, 1599, 1523, 1466, 1441 cm$^{-1}$
$^1$H NMR (CDCl$_3$) δ 0.89 (3H, t, J=7.5 Hz), 1.60–1.83 (2H, m), 3.88 (2H, t, J=7.2 Hz), 6.61 (1H, d, J=9.3 Hz), 7.06–7.35 (4H, m), 7.35–7.60 (2H, m), 7.96 (1H, d, J=4.8 Hz), 8.42 (1H, dd, J=4.8, 1.4 Hz), 9.05 (1H, d, J=1.4 Hz)
APCI-MS m/z 349 (MH$^+$)

The invention claimed is:

1. A pyrazolopyrazine compound of the following formula (I):

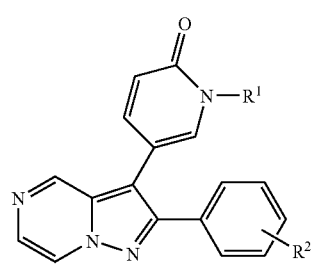

wherein

R$^1$ is hydrogen, lower alkyl, ar(lower)alkyl or cyclo(lower)alkyl which may be interrupted by an oxygen atom;

R$^2$ is hydrogen or halogen, or a salt thereof.

2. A process for the preparation of the pyrazolopyrazine compound of claim 1 or a salt thereof, which comprises, (1) hydrolyzing a compound of the formula (II):

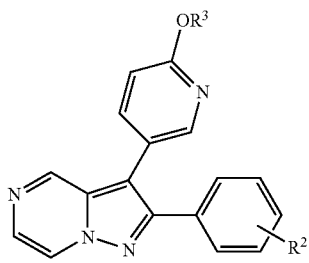

wherein
R² is hydrogen or halogen;
R³ is lower alkyl;
or a salt thereof,
to give a compound of the formula (Ia):

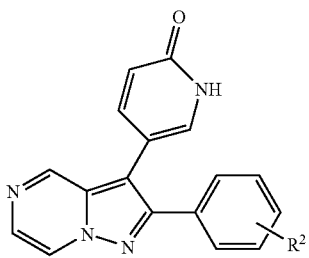

wherein R² is as defined above or a salt thereof,
(2) reacting a compound of the formula (Ia) or a salt thereof, with a compound of the formula (III):

R¹ᵃ—X    (III)

wherein R¹ᵃ is hydrogen, lower alkyl, ar(lower)alkyl or cyclo(lower)alkyl which may be interrupted by an oxygen atom;

X is a leaving group,
or a salt thereof
to give a compound of the formula (Ib):

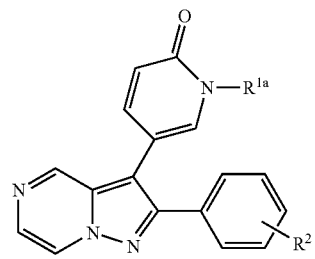

wherein R¹ᵃ and R² are as defined above or a salt thereof.

3. A pharmaceutical composition comprising the compound of claim 1 or a pharmaceutically acceptable salt thereof in admixture with a pharmaceutically acceptable carrier.

4. A method for treating a disease selected from the group consisting of depression, dementia, Parkinson's disease and anxiety, which comprises administering the compound of claim 1 or a pharmaceutically acceptable salt thereof to a human being or an animal in need thereof.

5. A process for preparing a pharmaceutical composition which comprises admixing the compound of claim 1 or a pharmaceutically acceptable salt thereof with a pharmaceutically acceptable carrier.

6. An in vitro method for evaluation of adenosine antagonism which comprises contacting the compound of claim 1 or a pharmaceutically acceptable salt thereof with a human $A_1$ or $A_{2a}$ receptor.

* * * * *